United States Patent

Zheng et al.

[11] Patent Number: 5,892,063
[45] Date of Patent: Apr. 6, 1999

[54] CEPHALOMANNINE EPOXIDE, ITS ANALOGUES AND A METHOD FOR PREPARING THE SAME

[75] Inventors: Qun Y. Zheng, Superior; Christopher K. Murray; Randall J. Daughenbaugh, both of Longmont, all of Colo.

[73] Assignee: Hauser, Inc., Boulder, Colo.

[21] Appl. No.: 861,286

[22] Filed: May 21, 1997

Related U.S. Application Data

[63] Continuation-in-part of Ser. No. 401,711, Mar. 10, 1995, abandoned.

[51] Int. Cl.⁶ .................................................. C07D 305/14
[52] U.S. Cl. ............................................. 549/510; 549/511
[58] Field of Search ...................................... 549/510, 511

[56] References Cited

PUBLICATIONS

"Status of the NCI Preclinical Antitumor Drug Discovery Screen," Michael R. Boyd, M.D., Ph.D., *Principles & Practices of Oncology* vol. 3, No. 10 (Oct. 1989).

"Data Display and Analysis Strategies for the NCI Disease–Oriented In Vitro Antitumor Drug Screen," M.R. Boyd, K.D. Paull and L.R. Rubinstein, *Proceedings of the Twenty–Second Annual Cancer Symposium,* Detroit Michigan, USA—Apr. 26–28, 1990, pp.11–34.

*Primary Examiner*—Ba K. Trinh
*Attorney, Agent, or Firm*—Chrisman, Bynum & Johnson; Steven C. Petersen

[57] ABSTRACT

An antitumor compound of formula (5)

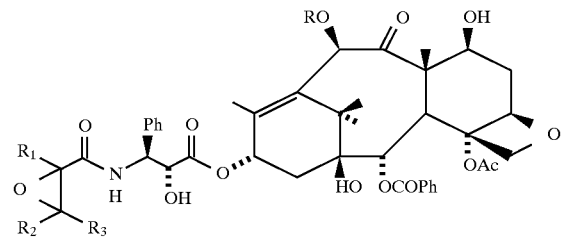

in which R is Ac or H, and $R_1$, $R_2$ is an alkyl group such as Me, Et, Pr, i-Pr, n-Bu or t-Bu, $R_3$ is H; $R_1$ and $R_2$ and $R_3$ are H; $R_1$ is an alkyl group such as Me, Et, Pr, i-Pr, n-Bu or t-Bu, $R_2$, $R_3$ is H; $R_1$ and $R_3$ are H, $R_2$ is an alkyl group such as Me, Et, Pr, i-Pr, n-Bu or t-Bu; $R_1$ is H, $R_2$ and $R_3$ are an alkyl group such as Me, Et, Pr, i-Pr, n-Bu or t-Bu; $R_1$ and $R_2$ and $R_3$ are an alkyl group Me, Et, Pr, i-Pr, n-Bu or t-Bu. Me is an abbreviation for methyl, Et is ethyl, Pr is propyl, i-Pr is isopropyl, n-Bu is n-butyl, and t-Bu is tert-butyl. Also provided by the invention is a one step method of preparing a compound of formula (5) whereby a taxane having a tiglate group attached to the side chain is contacted with an oxidizing reagent resulting in the formation of an epoxide having antitumor activity.

23 Claims, 9 Drawing Sheets

CEPHALOMANNINE EPOXIDE, ITS ANALOGUES AND A METHOD FOR PREPARING THE SAME

This application is a continuation-in-part of application Ser. No. 08/401,711, filed Mar. 10, 1995, now abandoned.

BACKGROUND OF THE INVENTION

1. Field of the Invention

The present invention relates to the preparation of cephalomannine epoxide and 10-DATB-epoxide from the precursors cephalomannine and 10-deacetyl taxol B (10-DATB), respectively. Specifically, the present invention relates to novel active antitumor agents that are formed when the tiglate structure located on the side chain of the aforementioned precursors is converted into an epoxide.

2. Description of the State of Art

Between the years 1958 and 1980, extracts of over 35,000 plant species were tested for anticancer activity as part of an NCI-sponsored program. Chemists Monroe E. Wall and M. C. Wani first isolated a crude extract concentrate from yew tree (*Taxus brevifolia*) bark and wood samples in 1963. Initial screening showed the extract to be a potential anti-cancer agent, being very active against an unusually wide range of rodent cancers. Isolation of the active agent in the crude extract took several years due to the very low concentrations of the agent present in the plants. The active agent was identified, the structure determined and the compound, in 1971, was named taxol, generically referred to as paclitaxel (1).

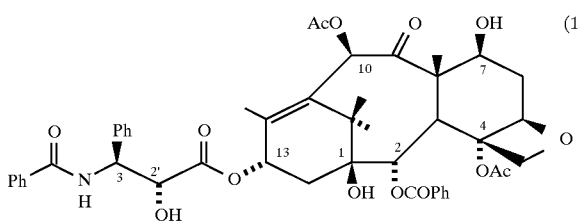

The naturally occurring diterpenoid, paclitaxel (1), is one of the most exciting discoveries in the field of cancer chemotherapy. In 1979, Susan B. Horwitz and co-workers established that, while paclitaxel was an antimiotic inhibitor, the mechanism was unique in that it stabilizes microtubules and inhibits depolymerization back to tubulin; this was quite the opposite effect of other antimiotic agents which all bind to soluble tubulin and inhibit the polymerization of tubulin to form microtubules. See, Nature 227:655–667 (1979). Thus, taxol increases the time required for cell division which in turn inhibits tumor activity.

Since the discovery of paclitaxel, over one hundred compounds having the taxane skeleton have been isolated from various Taxus species, listed below are but a few of the representative structures of the more notable taxol analogues.

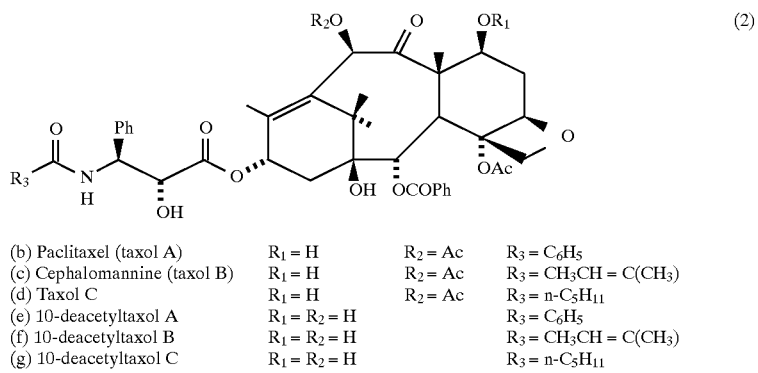

| | | | |
|---|---|---|---|
| (b) Paclitaxel (taxol A) | $R_1 = H$ | $R_2 = Ac$ | $R_3 = C_6H_5$ |
| (c) Cephalomannine (taxol B) | $R_1 = H$ | $R_2 = Ac$ | $R_3 = CH_3CH=C(CH_3)$ |
| (d) Taxol C | $R_1 = H$ | $R_2 = Ac$ | $R_3 = n\text{-}C_5H_{11}$ |
| (e) 10-deacetyltaxol A | $R_1 = R_2 = H$ | | $R_3 = C_6H_5$ |
| (f) 10-deacetyltaxol B | $R_1 = R_2 = H$ | | $R_3 = CH_3CH=C(CH_3)$ |
| (g) 10-deacetyltaxol C | $R_1 = R_2 = H$ | | $R_3 = n\text{-}C_5H_{11}$ |

Despite paclitaxel's excellent activity in model tumor systems, research progressed at a rather a slow pace and its development was fraught with many obstacles including scarcity of the drug (owing to low abundance of Yew tissue), extremely low aqueous solubility, and toxicities. Problems in drug supply have largely been alleviated, not only as a result of more efficient collection and extraction of plant material, but also because of the progress made in the complete and semi-synthesis of the compound paclitaxel; however, the extremely low aqueous solubility and toxicity obstacles remain more difficult to overcome.

Paclitaxel is a complex diterpenoid which comprises of a bulky, fused ring system and an extended side chain at the C-13 position that is required for activity. This complex structure further contains 11 chiral centres with 2048 possible diastereoisomeric forms. Relatively hydrophilic domains exist in the molecule around the vicinity of the C-7 through C-10 and C-1' through C-2' positions. However, hydrophobic domains of the taxane backbone and side chain contribute to the overall poor aqueous solubility of the compound. In order to administer human doses in a reasonable volume, paclitaxel is currently formulated for clinical use in a mixture of anhydrous ethanol and polyethoxylated castor oil (Cremophor EL®), a clear, oily, viscous, yellow surfactant. In addition to the potential problems of physical instability, the most significant problem with the current clinical paclitaxel formulation is that the Cremophor EL® vehicle possesses pharmacological activity. While a variety of drugs are administered in Cremophor EL®, the dose of Cremophor EL® that accompanies a dose of paclitaxel is the highest for any marketed drug. Cremophor EL® has been observed to cause serious or fatal hypersensitivity episodes, and vehicle toxicity may be largely responsible for fatal or life-threatening anaphylactoid reactions observed upon rapid infusion of paclitaxel into animals or humans.

In light of the serious risks associated with the current intravenous formulations of paclitaxel, efforts to develop safe, convenient, and efficacious paclitaxel formulations are ongoing. However, the majority of approaches underway to solve the problems associated with paclitaxel are the synthesis and evaluation of a second generation of paclitaxel analogues.

10-deacetylbaccatin III (2) and baccatin III (3)

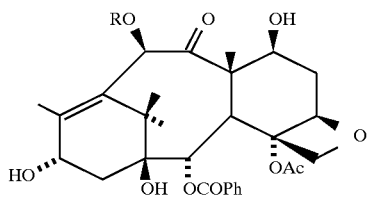

10-deacetyl baccatin III, R=H (2)

baccatin III, R=Ac (3)

are diterpenes that are more readily available than paclitaxel and are known synthetic precursors of paclitaxel and its analogues. Their structural complexity is less than that of paclitaxel's and therefore, 10-deacetylbaccatin III (2) and baccatin III (3) are also valuable starting materials for structural modifications at the diterpene part of the paclitaxel molecule.

10-deacetylbaccatin III was used as the starting material for the semisynthetic compound docetaxel (4) commonly referred to as Taxotère®, developed by French researchers from the Institut de Chèmie de Substances Naturelles and Rhône-Poulenc Rorer in 1981.

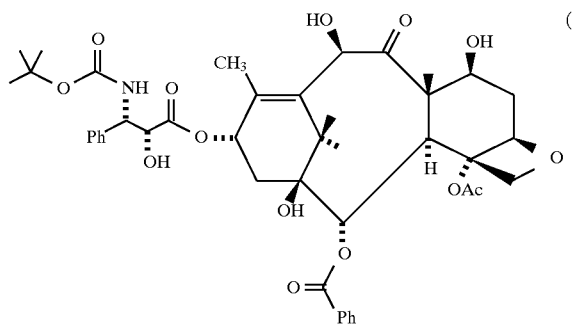

The lateral side chain located at C-13 position, which is responsible for its cytoxic effect, is added chemically. Docetaxel differs structurally from paclitaxel at the C-10 position on the baccatin ring and at the C-3' position on the lateral side chain. See, "Biologically Active Taxol Analogues with Deleted A-Ring Side Chain Substitueants and Variable C-2' Configuration," J. Med. Chem., 34:1176–1184 (1991); "Relationships between the Structure of Taxol Analogues and Their Antimitotic Activity," J. Med. Chem., 34:992–998 (1991). Docetaxel is twice as potent an inhibitor of microtubule depolymerization as paclitaxel. The in vitro cytotoxicity of docetaxel in murine and human tumor cell lines and its in vivo preclinical activity in murine and human xenografts have been impressive. Docetaxel has displayed higher cytoxic activity than other antineoplastic agents such as paclitaxel, cisplatin, cyclophosphamide, and doxorubicin against the same tumor models. While docetaxel is a promising antitumor agent with a broad spectrum it, like paclitaxel, suffers low aqueous solubility. The fact remains however, that a potent analogue of paclitaxel having promising activity was developed by making a simple side chain modifications at the 3' amide. Encouraged by this exciting result other researchers began modifications to each position of the diterpene core hoping to develop a structural analogue of paclitaxel which overcomes the problems associated with paclitaxel; however, to date, non have been developed.

There is still a need, therefore, for developing structural analogues of paclitaxel which have less formulation problems and equivalent or greater potency than that of paclitaxel.

SUMMARY OF THE INVENTION

Accordingly, it is an object of this invention to provide structural analogues of taxol which demonstrate antitumor activity and a method for the preparation of the same. More specifically the present invention provides taxol derivatives having antitumor activity of formula (5)

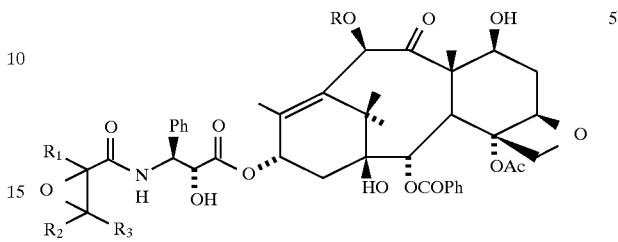

in which R=an acetyl group (Ac) or hydrogen (H), and $R_1=R_2=$an alkyl group such as Me, Et, Pr, i-Pr, n-Bu or t-Bu, $R_3=H$; $R_1=R_2=R_3=H$; $R_1=$an alkyl group such as Me, Et, Pr, i-Pr, n-Bu or t-Bu, $R_2=R_3=H$; $R_1=R_3=H$, $R_2=$an alkyl group such as Me, Et, Pr, i-Pr, n-Bu or t-Bu; $R_1=H$, $R_2=R_3=$an alkyl group such as Me, Et, Pr, i-Pr, n-Bu or t-Bu; $R_1=R_2=R_3=$an alkyl group Me, Et, Pr, i-Pr, n-Bu or t-Bu. Me is an abbreviation for methyl, Et is ethyl, Pr is propyl, i-Pr is isopropyl, n-Bu is n-butyl, and t-Bu is tert-butyl.

Another object of the present invention is to provide a method for the preparation of cephalomannine epoxide and its analogues.

A further object of the present invention is to provide a method for the preparation of 10-deacetyl taxol B epoxide and its analogues.

Additional objects, advantages and novel features of this invention shall be set forth in part in the description and examples that follow, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein the method, and compositions produced thereby, of this invention comprises contacting a taxane compound having a tiglate group attached to the side chain with an oxidizing reagent resulting in the oxidation of the tiglate group, that is, the formation of an epoxide having antitumor activity.

BRIEF DESCRIPTION OF THE DRAWINGS

The accompanying drawings, which are incorporated in and form a part of the specification, illustrate the preferred embodiments of the present invention, and together with the description serve to explain the principles of the invention.

In all of the drawings which follow, the horizontal axis depicts various dilutions of the test compound, ranging from $10^{-4}$ to $10^{-14}$ molar, that were exposed to a specified cancer. The vertical axis (percentage growth) depicts the growth of the specified cancer cell line when exposed to a specific concentration of the tested compound as compared to the growth of the same cancer cell line not exposed to any compound.

DETAILED DESCRIPTION OF THE PREFERRED EMBODIMENT

Figure 1A:
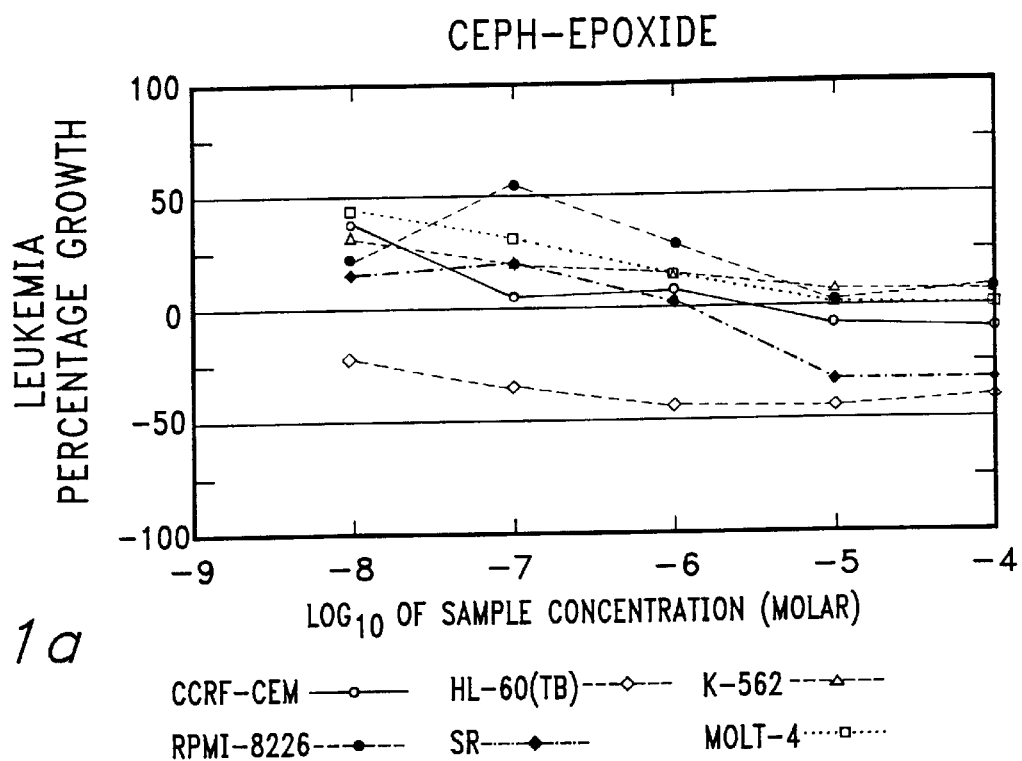
FIG. 1a depicts the dose response curves generated by exposing various leukemia cell lines to various concentrations of the composition of the present invention.

The present invention provides novel taxol derivatives of formula (5)

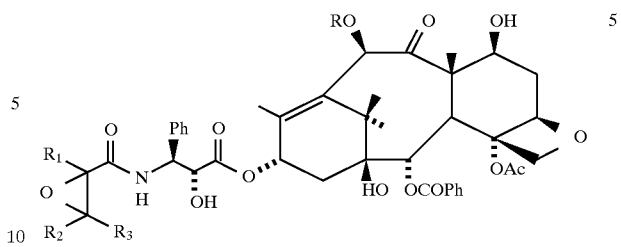

in which R=an acetyl group (Ac) or a hydrogen (H), and $R_1=R_2=$an alkyl group such as Me, Et, Pr, i-Pr, n-Bu or t-Bu, $R_3=$H; $R_1=R_2=R_3=$H; $R_1=$an alkyl group such as Me, Et, Pr, i-Pr, n-Bu or t-Bu, $R_2=R_3=$H; $R_1=R_3=$H, $R_2=$an alkyl group such as Me, Et, Pr, i-Pr, n-Bu or t-Bu; $R_1=$H, $R_2=R_3=$an alkyl group such as Me, Et, Pr, i-Pr, n-Bu or t-Bu; $R_1=R_2=R_3=$an alkyl group Me, Et, Pr, i-Pr, n-Bu or t-Bu. Me is an abbreviation for Methyl, Et is ethyl, Pr is propyl, i-Pr is isopropyl, n-Bu is n-Butyl, and t-Bu is tert-Butyl.

The synthesis of a compound of formula 5 can be accomplished by a wide variety of methods. The synthetic descriptions and specific examples that follow are only intended for the purposes of illustration, and are not to be construed as limiting in any manner to make compounds of the present invention by other methods.

In one embodiment a compound of formula 5, wherein R=Ac or H, and $R_1=R_2=$Me, $R_3=$H; may be made by reacting an oxidizing reagent, such as, monoperoxyphthalic acid magnesium salt hexahydrate (MMPP) or 3-chloroperoxybenzoic acid (MCPBA) with a compound of formula 1b:

in which R represents acetyl (cephalomannine) or hydrogen (10-deacetyl taxol B), in an organic solvent such as tetrahydofuran, methylene chloride, or chloroform at 0–50° C. for a period of 12–72 hours to produce an epoxide or a compound of formula (5).

The diostereomers from ceph-epoxide or 10-DATB-epoxide obtained by the embodiment discussed above can be separated by physicochemical methods such as chromatography.

To determine the cytotoxicity of ceph-epoxide as compared to taxol screening assays were performed; these activities are summarized in Table I (set out below). The screening assay is performed on 96-well microtitre plates. Relatively high initial inoculation densities are used, in order to permit measurement of "time-zero" values and to enhance the screen's ability to detect and provide some differentiation between antiproliferative and cytotoxic response parameters. The specific inoculation densities (which range from 5,000 to 40,000 cells/well) used for each cell line are those which, for the respective line, were determined to give an optical density signal for both the "time-zero" value (at 24 hours) and the "no-drug" control (at 72 hours) above the noise level and within the linear range of the end-point assay (which measures cellular protein). The inoculated microtitre plates are pre-incubated for 24 hours at 37° C. prior to drug additions. The five drug dilutions tested routinely range from $10^{-4}$ to $10^{-8}$ molar.

Higher or lower concentration ranges may be selected on a nonroutine basis if appropriate solubility and/or prior biological information or other screening data so dictate. Duplicate wells are prepared for all concentrations; "time-zero" and "nodrug" controls are also provided for each test. The minimum amount of compound required for a 1-time evaluation in the routine screen can be calculated from the knowledge that each test requires a total of approximately 40 ml (0.04 liter) of cell culture medium containing the highest desired drug concentration. Thus, the amount (grams) of sample required (assuming an upper test concentration limit of $10^{-4}$M) is: molecular weight of compound×$10^{-4}$×0.04. After a 48 hour incubation (37° C.) with the test compound, the cells are fixed in situ to the bottoms of the microtitre wells by addition of 50 μl of either 50% trichloroacetic acid (for adherent cell lines) or 80% trichloroacetic acid (for settled cell suspension lines), followed by incubation for 60 minutes at 4° C. The cellular protein in each well is assayed using a sulforhodamine B (SRB) stain procedure. Briefly, after discarding the supernatants, the microtitre plates are washed 5 times with deionized water and air-dried. One hundred microliters of SRB solution (0.4% w/v in 1% acetic acid) is added to each microtitre well and incubated for 10 minutes at room temperature. Unbound SRB is removed by washing 5 times with 1% acetic acid. The plates are air-dried, the bound stain is solubilized with Tris buffer, and the optical densities read at 515 nm. SRB is a bright pink anionic dye which, in dilute acetic acid, binds electrostatically to the basic amino acids of TCA-fixed cells. Cryopreserved master stocks of all the lines are maintained, and cultures used for screening are replaced from the master stock after no more than twenty passages in the screening laboratory. The cell line panel consists of 60 lines, organized into nine, disease-related subpanels including leukemia, non-small-cell lung cancer, colon, CNS, melanoma, ovarian, renal, prostate and breast cancers.

The response parameters $GI_{50}$ and $LC_{50}$ are interpolated values representing the concentrations at which the percentage growth (PG) is +50 and −50 respectively:

$GI_{50}$ is the concentration for which the PG=+50. At this value the increase from time $t_{zero}$ in the number or mass of cells in the test well is only 50% as much as the corresponding increase in the control well during this period of the experiment. A drug effect of this intensity is interpreted as primary growth inhibition.

TGI is the concentration for which PG=0. At this value the number or mass of cells in the well at the end of the experiment equals the number or mass of cells in the well at time $t_{zero}$. A drug effect of this intensity is regarded as cytostasis.

$LC_{50}$ is the concentration for which the PG=−50. At this value, the number or mass of cells in the test well at the end of the experiment is half that at time $t_{zero}$. This is interpreted as cytotoxicity.

TABLE I

| Panel/ | $Log_{10}$ $GI_{50}$ | | $Log_{10}$ TGI | | $Log_{10}$ $LC_{50}$ | |
|---|---|---|---|---|---|---|
| Cell line | Ceph-epoxide | Paclitaxel | Ceph-epoxide | Paclitaxel | Ceph-epoxide | Paclitaxel |
| Leukemia | | | | | | |
| CCRF-CEM | <−8.00 | −11.61 | −5.60 | >−4.00 | >−4.00 | >−4.00 |
| HL-60(TB) | <−8.00 | −11.57 | <−8.00 | >−4.53 | >−4.00 | >−4.00 |
| K-562 | <−8.00 | −10.83 | >−4.00 | >−4.00 | >−4.00 | >−4.00 |
| MOLT-4 | <−8.00 | −11.07 | >−4.00 | >−4.00 | >−4.00 | >−4.00 |
| RPMI-8226 | — | <−13.00 | >A.00 | >−4.00 | >−4.00 | >−4.00 |
| SR | <−8.00 | −8.34 | 5.94 | >−4.00 | >−4.00 | >−4.00 |
| Non-Small Cell Lung Cancer | | | | | | |
| HOP-62 | −7.61 | −9.67 | — | −4.80 | >−4.00 | −4.10 |
| NCI-H322M | −7.62 | −10.12 | >−4.00 | −4.46 | >−4.00 | >−4.00 |
| NCI-H460 | <−8.00 | −12.16 | >−4.00 | "4.92 | >−4.00 | >−4.00 |
| NCI-H522 | <−8.00 | <−13.00 | −7.48 | −11.20 | — | >−4.00 |
| Colon Cancer | | | | | | |
| COLO 205 | <−8.00 | −11.07 | −7.57 | — | −6.22 | >−4.41 |
| HCC-2998 | <−8.00 | −12.34 | −7.34 | −4.77 | >−4.00 | −4.26 |
| HCT-116 | <−8.00 | <−13.00 | — | −4.82 | >−4.00 | >−4.00 |
| HCT-15 | −6.22 | −6.37 | >−4.00 | >−4.00 | >−4.00 | >−4.00 |
| HT29 | <−8.00 | <−13.00 | −6.94 | — | >−4.00 | −4.39 |
| KM12 | <−8.00 | −11.43 | — | −4.36 | >A.00 | >−4.00 |
| SW-620 | — | −11.60 | >−4.00 | >−4.00 | >−4.00 | >−4.00 |
| CNS Cancer | | | | | | |
| SF-539 | <−8.00 | −11.09 | <−8.00 | — | −7.39 | >−4.00 |
| SNB-19 | −7.59 | −8.98 | >−4.00 | >−4.00 | >−4.00 | >−4.00 |
| SNB-75 | <−8.00 | — | −7.82 | — | >−4.00 | — |
| U251 | <−8.00 | −11.29 | 6.85 | −4.32 | >−4.00 | −4.15 |
| Melanoma | | | | | | |
| LOX-IMVI | <−8.00 | −11.80 | −4.67 | −4.65 | >−4.00 | >−4.15 |
| MALME-3M | — | — | >−4.00 | −4.46 | >−4.00 | −4.11 |
| M14 | <−8.00 | −11.73 | — | −4.62 | >−4.00 | −4.13 |
| SK-MEL-2 | <−8.00 | −9.53 | — | — | >−4.00 | >−4.00 |
| UACC-257 | −7.68 | −10.30 | >−4.00 | −4.52 | >−4.00 | −4.03 |
| UACC-62 | <−8.00 | −10.46 | >−4.00 | "4.71 | >−4.00 | −4.19 |
| Ovarian Cancer | | | | | | |
| IGROV1 | <−8.00 | −8.61 | — | −4.19 | >−4.00 | >−4.00 |
| OVCAR-3 | <−8.00 | −10.40 | −7.74 | −4.55 | >−4.00 | >−4.00 |

TABLE I-continued

| Panel/ | Log₁₀ GI₅₀ | | Log₁₀ TGI | | Log₁₀ LC₅₀ | |
|---|---|---|---|---|---|---|
| Cell line | Ceph-epoxide | Paclitaxel | Ceph-epoxide | Paclitaxel | Ceph-epoxide | Paclitaxel |
| OVCAR-4 | −5.41 | −5.00 | >−4.00 | −4.19 | >−4.00 | >−4.00 |
| OVCAR-5 | −7.56 | −9.38 | −5.32 | −4.92 | >−4.00 | >−4.00 |
| OVCAR-8 | −7.80 | −10.75 | >−4.00 | — | >−4.00 | >−4.00 |
| Renal Cancer | | | | | | |
| 786-0 | −7.82 | −8.01 | >−4.00 | >−4.00 | >−4.00 | >−4.00 |
| A498 | −6.50 | −7.14 | >−4.00 | — | >−4.00 | −4.13 |
| RXF-393 | −6.67 | −8.32 | >−4.00 | −4.90 | >−4.00 | −4.45 |
| SN12C | <−8.00 | −9.53 | >−4.00 | −4.04 | >−4.00 | >−4.00 |
| TK-10 | −7.19 | −7.89 | >−4.00 | >−4.00 | >−4.00 | >−4.00 |
| UO-31 | −5.70 | −6.09 | >−4.00 | −4.29 | >−4.00 | >−4.00 |
| Prostate Cancer | | | | | | |
| PC-3 | −7.95 | −10.85 | >−4.00 | >−4.00 | >−4.00 | >−4.00 |
| DU-145 | −7.58 | −9.38 | −6.84 | >−4.00 | >−4.00 | >−4.00 |
| Breast Cancer | | | | | | |
| MCF7 | <−8.00 | −11.69 | >−4.00 | −4.05 | >−4.00 | >−4.00 |
| MCF7/ADR-RES | −4.86 | −8.48 | −4.21 | >−4.00 | >−4.00 | >−4.00 |
| MDA-MB-231/ATCC | −7.74 | −8.54 | — | −4.84 | >−4.00 | −4.29 |
| HS 578T | <−8.00 | — | −7.26 | — | >−4.00 | — |
| MDA-MB-435 | <−8.00 | <−13.00 | <−8.00 | — | — | — |
| MDA-N | <−8.00 | <−13.00 | <−8.00 | — | <−8.00 | — |
| BT-549 | −8.00 | −9.31 | −7.01 | −6.32 | <−4.00 | >−4.00 |
| T-47D | −4.81 | −9.81 | >−4.00 | −4.05 | >−4.00 | >−4.00 |
| Mean | −7.54 | −10.15 | −5.24 | −4.54 | −4.19 | −4.06 |
| Range | 3.19 | 8.00 | 4.00 | 7.20 | 4.00 | 0.45 |

The epoxides of the present invention in most instances are as potent and in some instances more potent than paclitaxel. The data represented in Table I is graphically represented in FIGS. 1a and 1b through FIGS. 9a and 9b. Dose response curves, depicted in the above mentioned Figures, are obtained by exposing various cancer cell lines to compounds that have a known concentration ($[\log_{10}M]$), as discussed in detail above, and then plotting the percentage growth of each cell line at each concentration. Percentage growth is determined by dividing the number or mass of cells in the test well by the number or mass of the cell in a control well. The following is an example of how the information in Table I and in the Figures is interpreted.

Figure 1B:
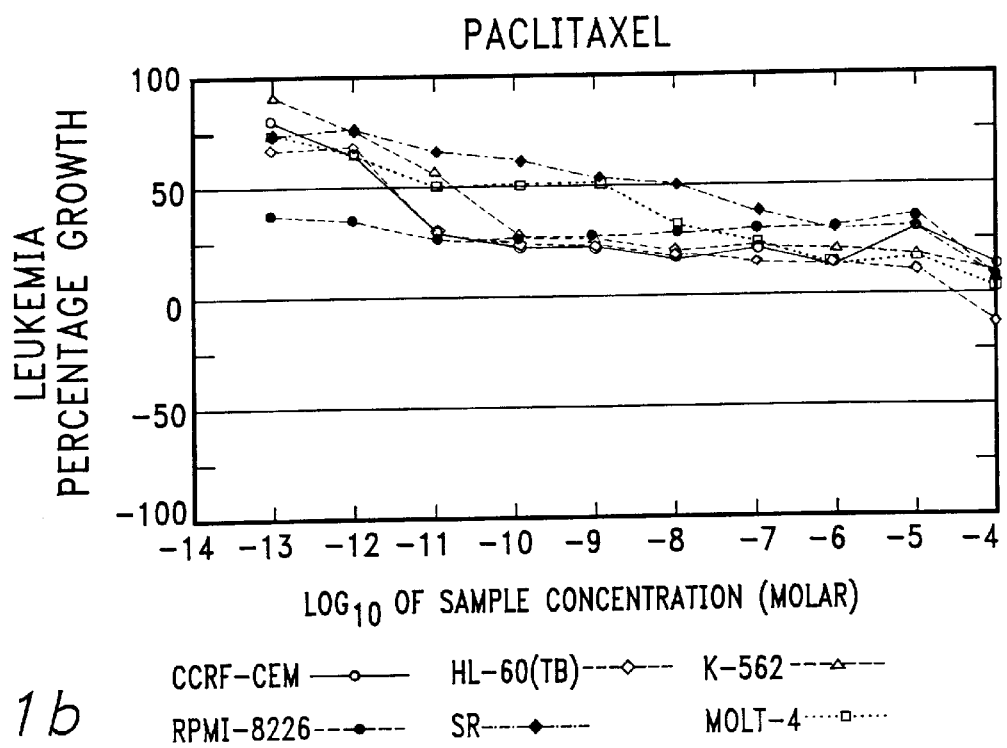
FIG. 1b depicts the dose response curves generated by exposing various leukemia cell lines to various concentrations of paclitaxel.
Figure 2A:
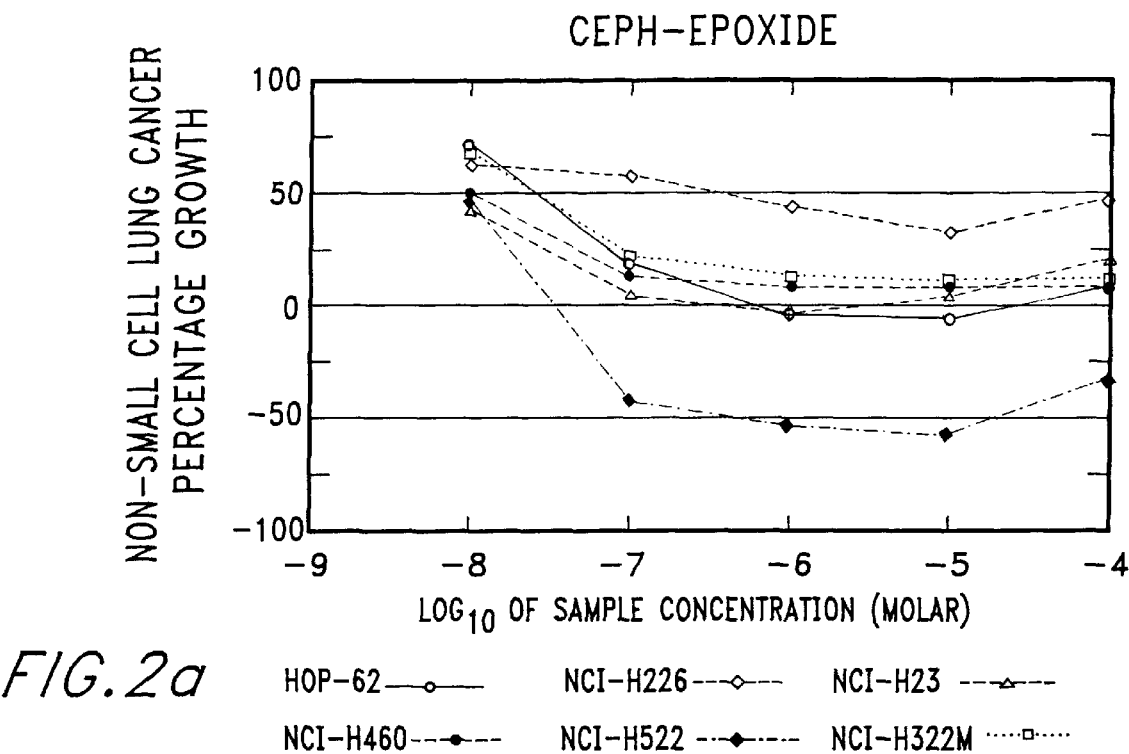
FIG. 2a depicts the dose response curves generated by exposing various non-small cell lung cancer cell lines to various concentrations of the composition of the present invention.
Figure 2B:
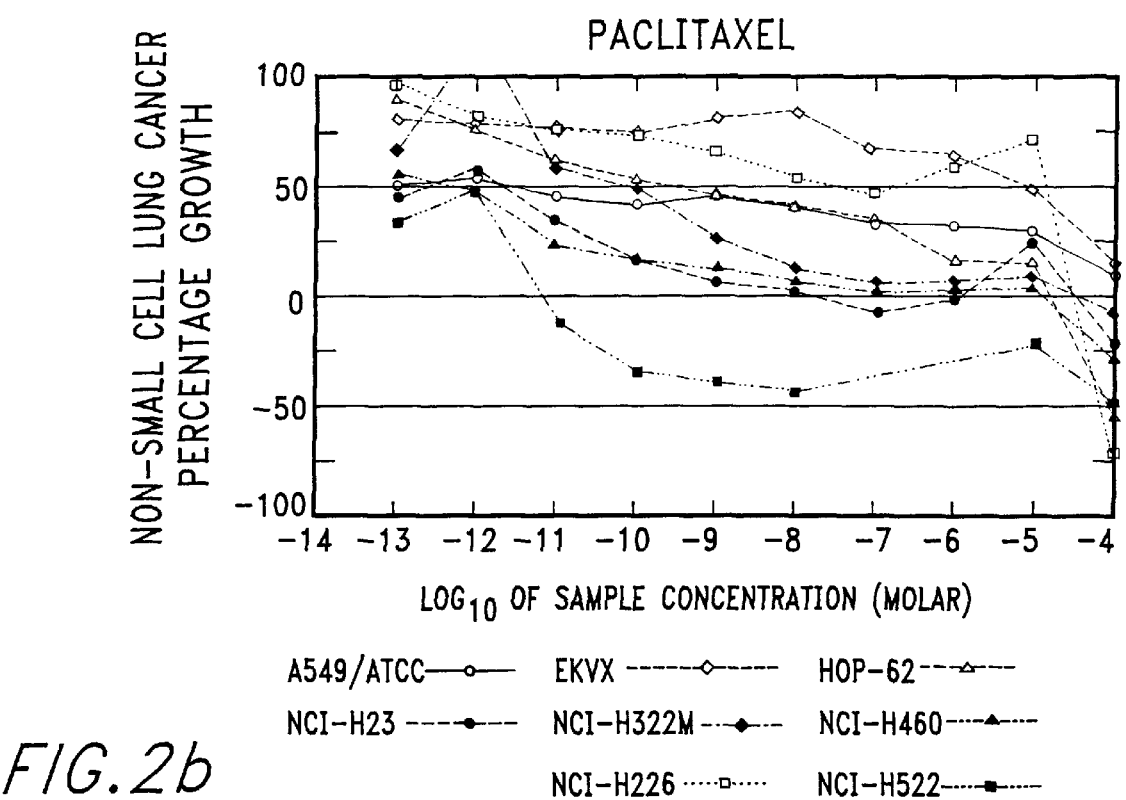
FIG. 2b depicts the dose response curves generated by exposing various non-small cell lung cancer cell lines to various concentrations of paclitaxel.
Figure 3A:
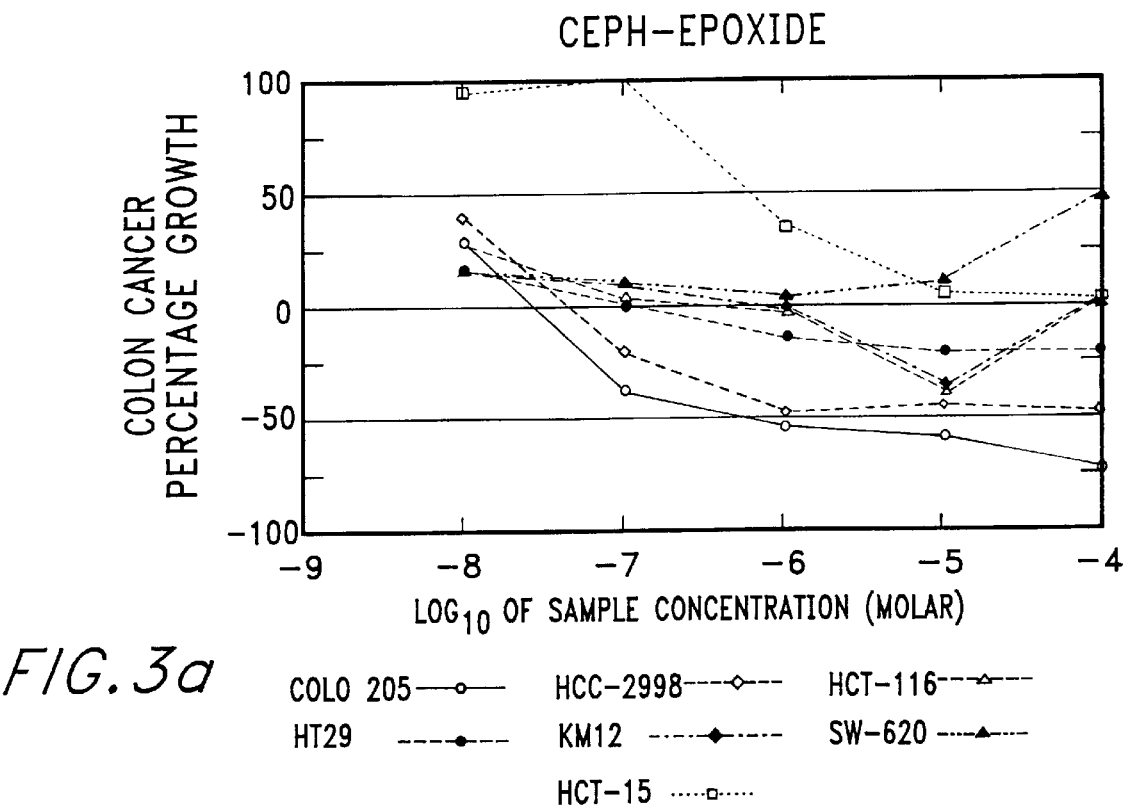
FIG. 3a depicts the dose response curves generated by exposing various colon cancer cell lines to various concentrations of the composition of the present invention.
Figure 3B:
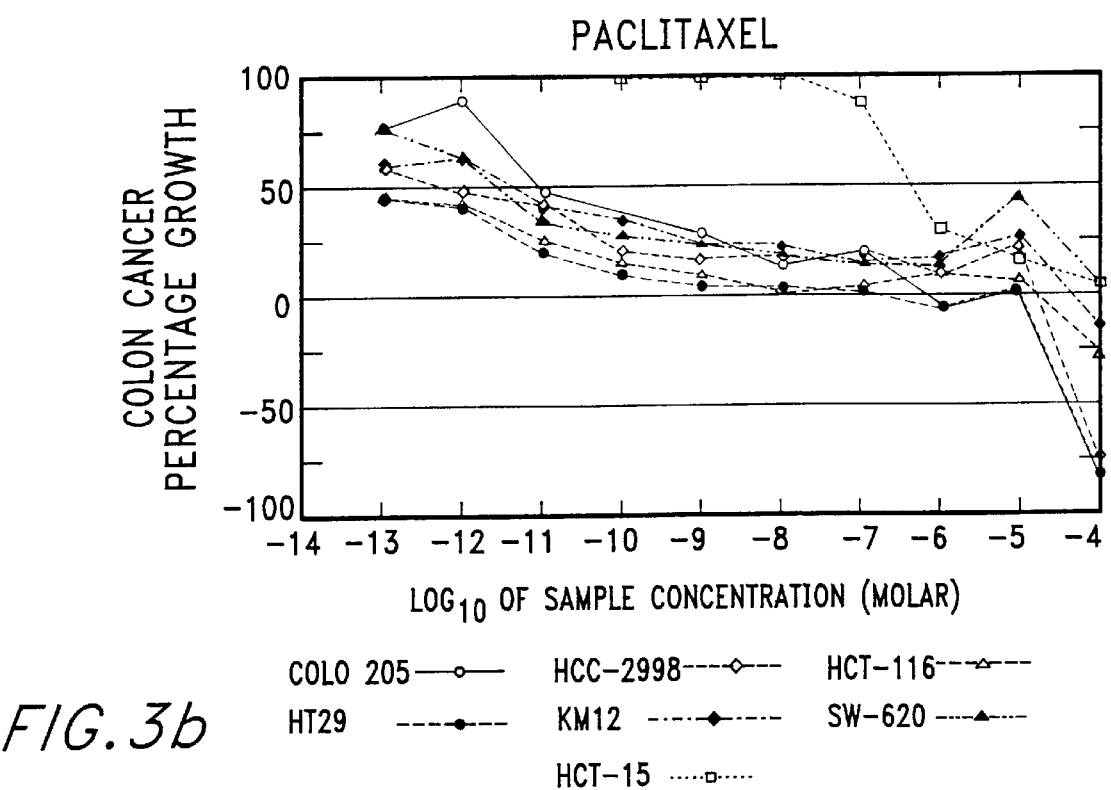
FIG. 3b depicts the dose response curves generated by exposing various colon cancer cell lines to various concentrations of paclitaxel.
Figure 4A:
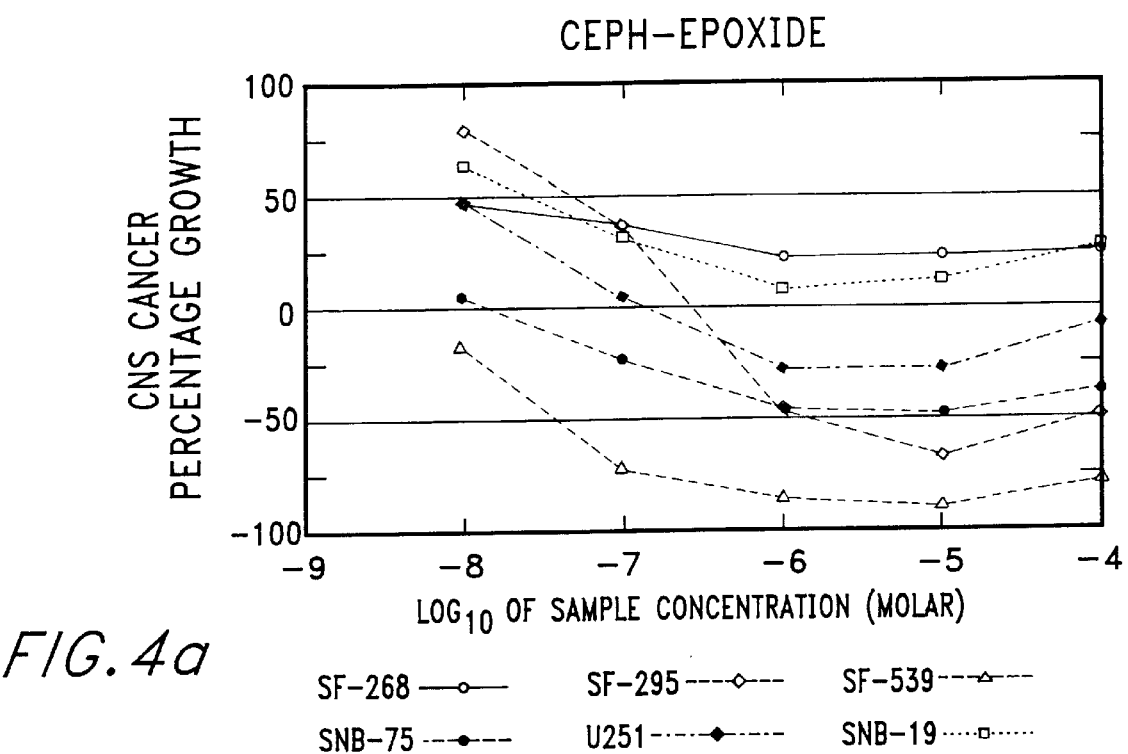
FIG. 4a depicts the dose response curves generated by exposing various CNS cancer cell lines to various concentrations of the composition of the present invention.
Figure 4B:
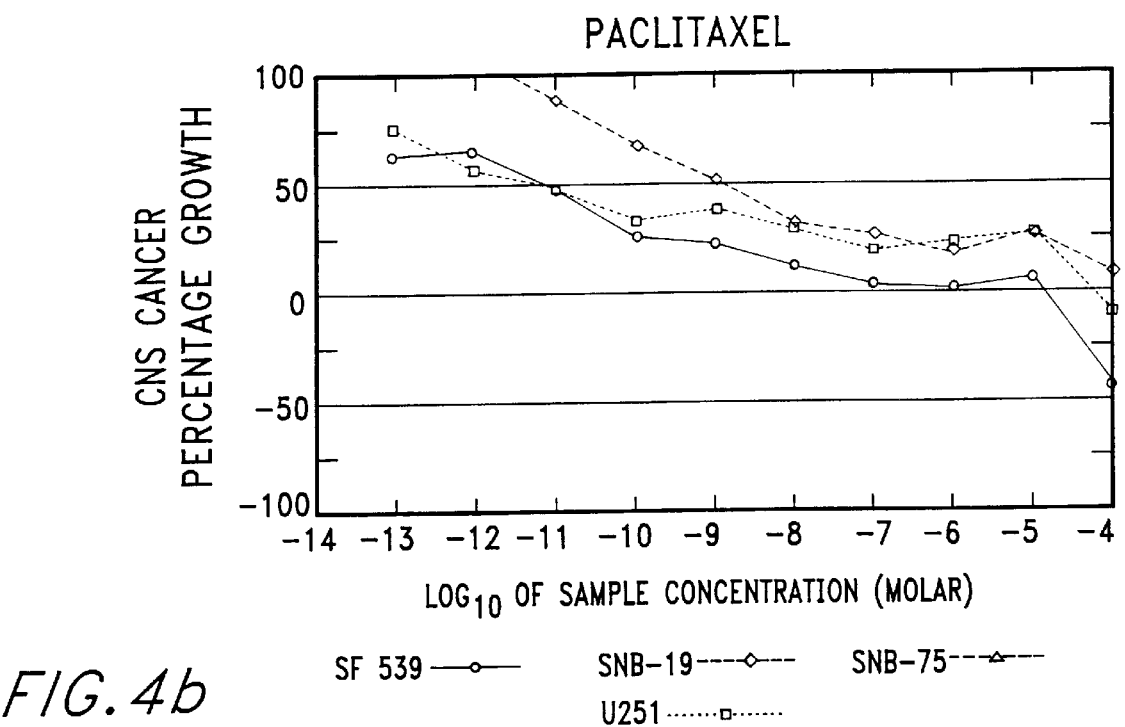
FIG. 4b depicts the dose response curves generated by exposing various CNS cancer cell lines to various concentrations of paclitaxel.
Figure 5A:
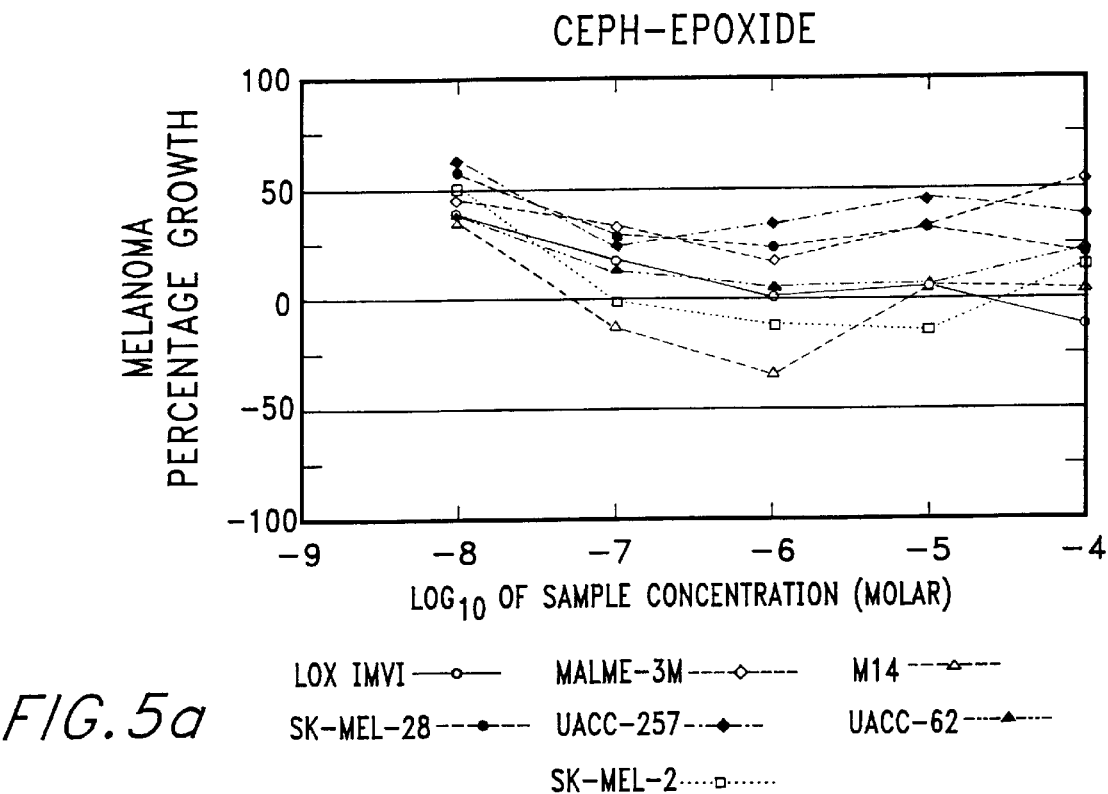
FIG. 5a depicts the dose response curves generated by exposing various melanoma cell lines to various concentrations of the composition of the present invention.
Figure 5B:
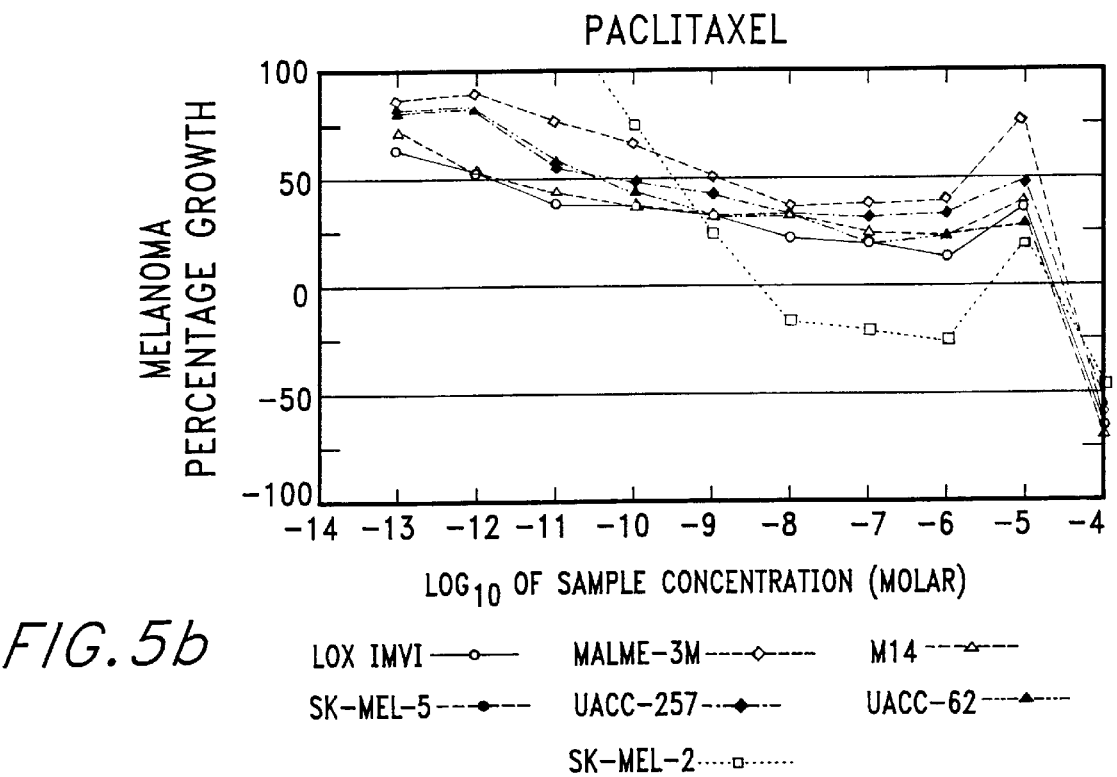
FIG. 5b depicts the dose response curves generated by exposing various melanoma cell lines to various concentrations of paclitaxel.
Figure 6A:
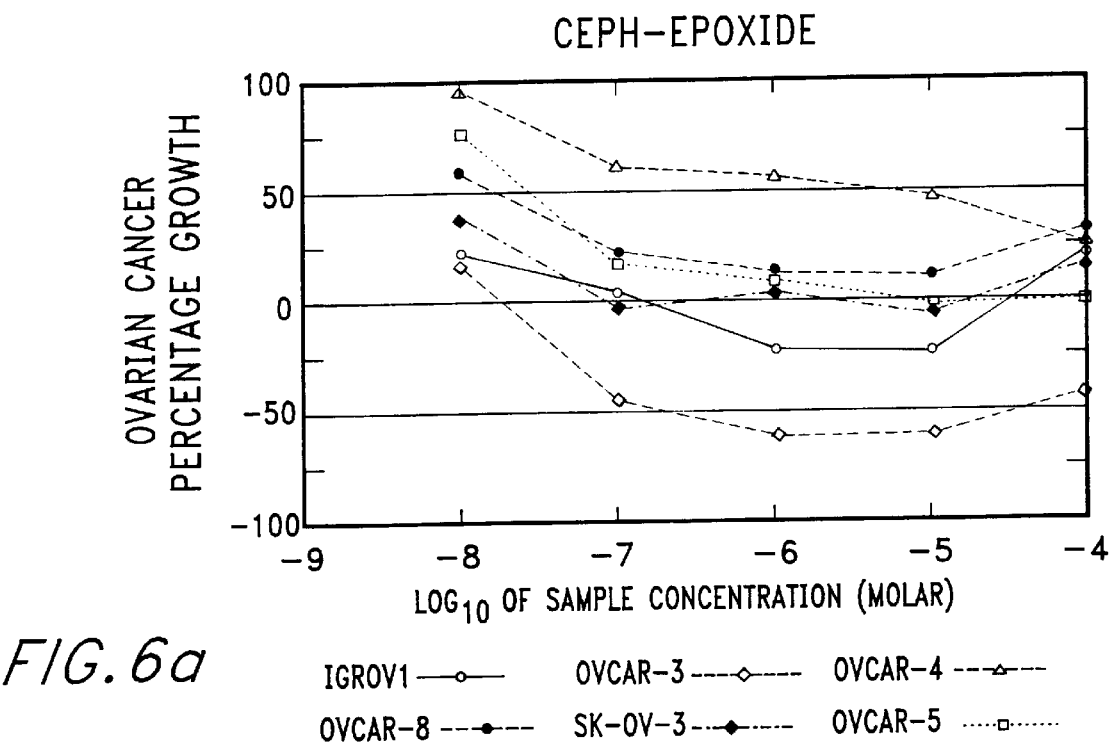
FIG. 6a depicts the dose response curves generated by exposing various ovarian cancer cell lines to various concentrations of the composition of the present invention.
Figure 6B:
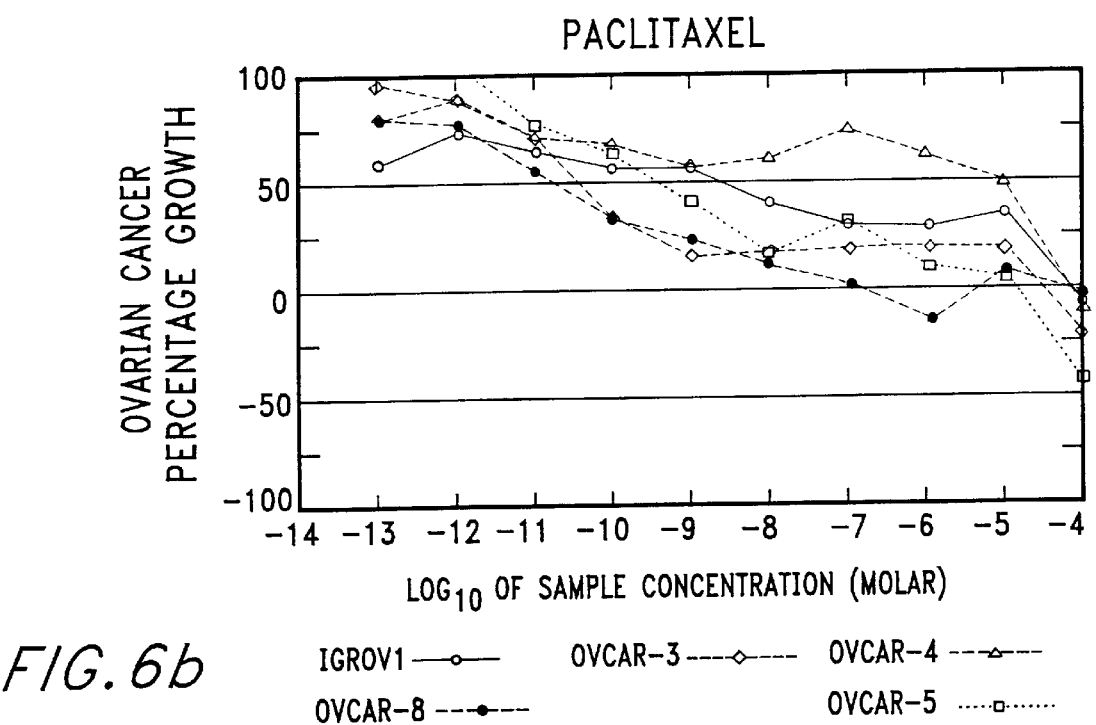
FIG. 6b depicts the dose response curves generated by exposing various ovarian cancer cell lines to various concentrations of paclitaxel.
Figure 7A:
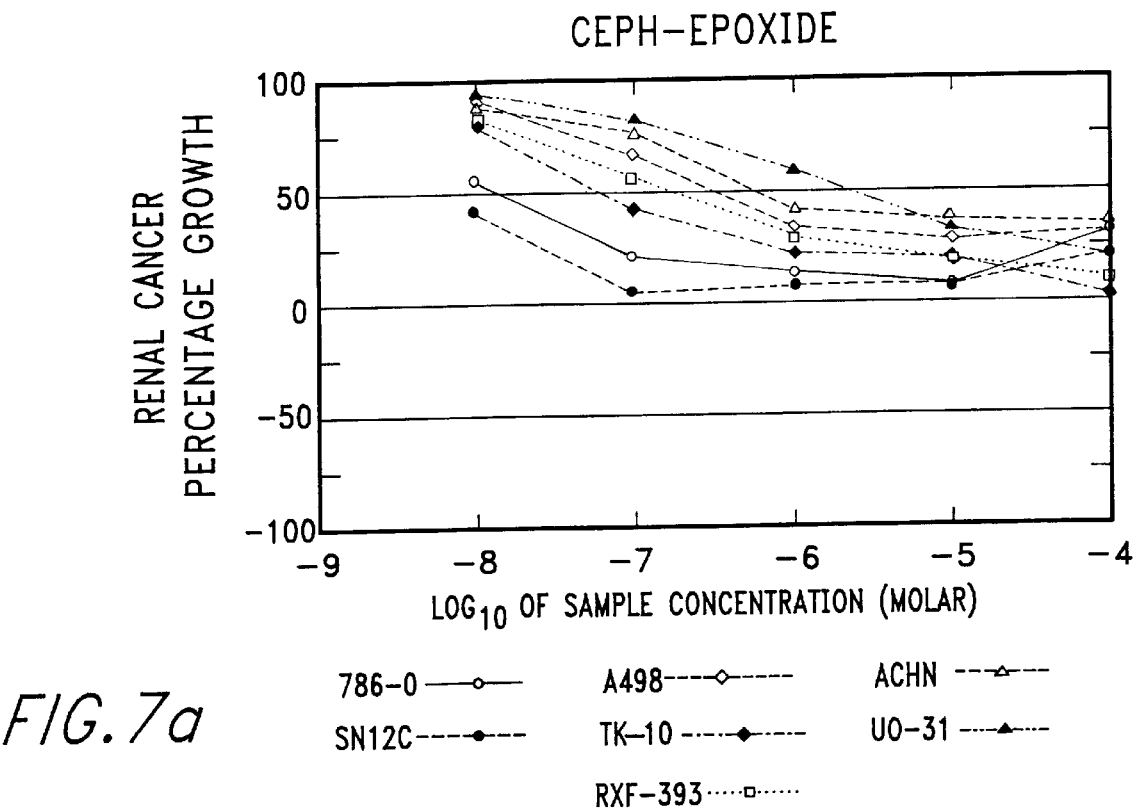
FIG. 7a depicts the dose response curves generated by exposing various renal cancer cell lines to various concentrations of the composition of the present invention.
Figure 7B:
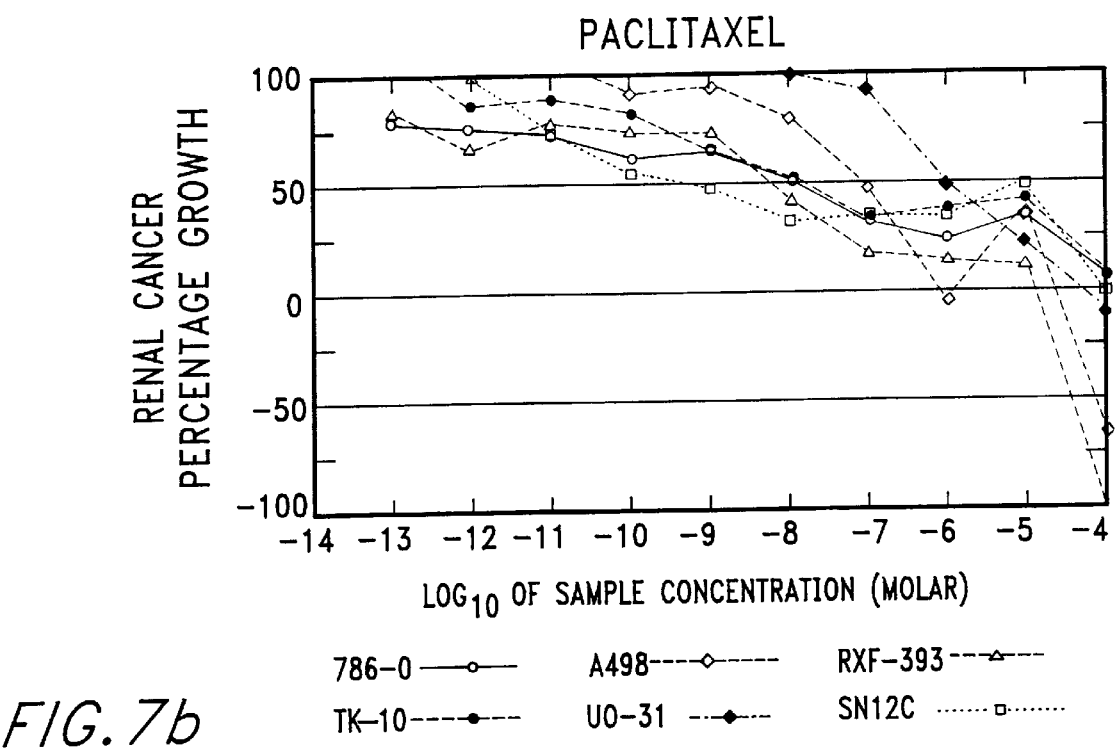
FIG. 7b depicts the dose response curves generated by exposing various renal cancer cell lines to various concentrations of paclitaxel.
Figure 8A:
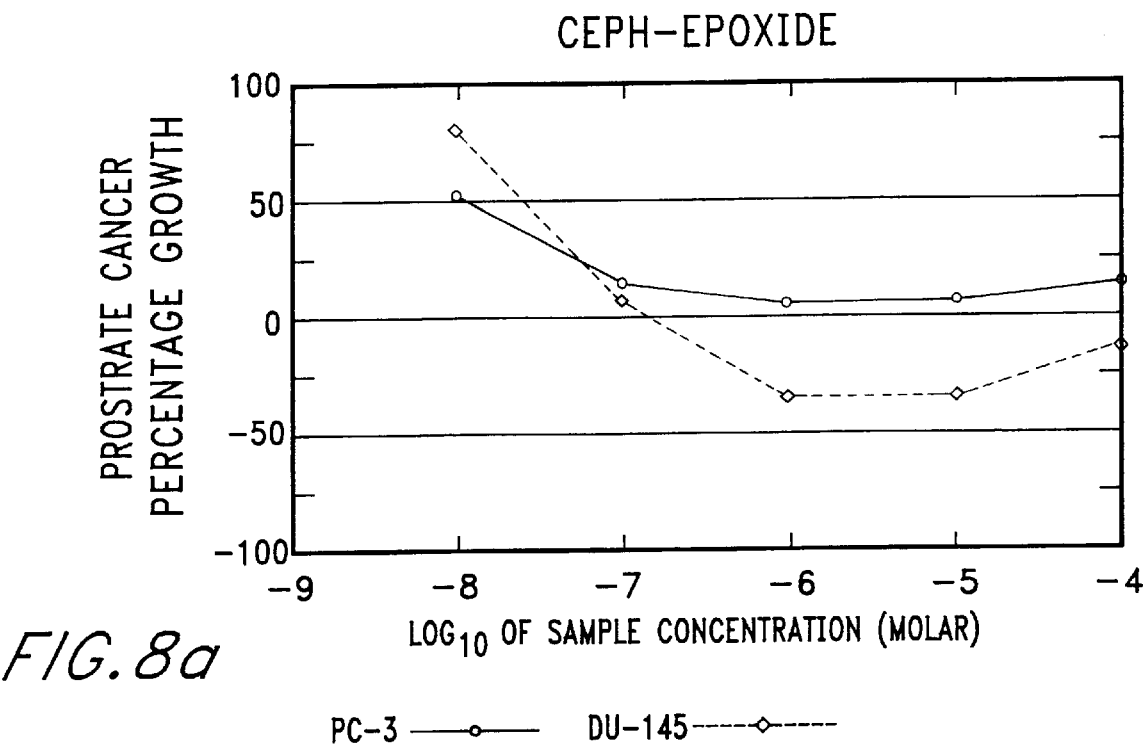
FIG. 8a depicts the dose response curves generated by exposing various prostate cancer cell lines to various concentrations of the composition of the present invention.
Figure 8B:
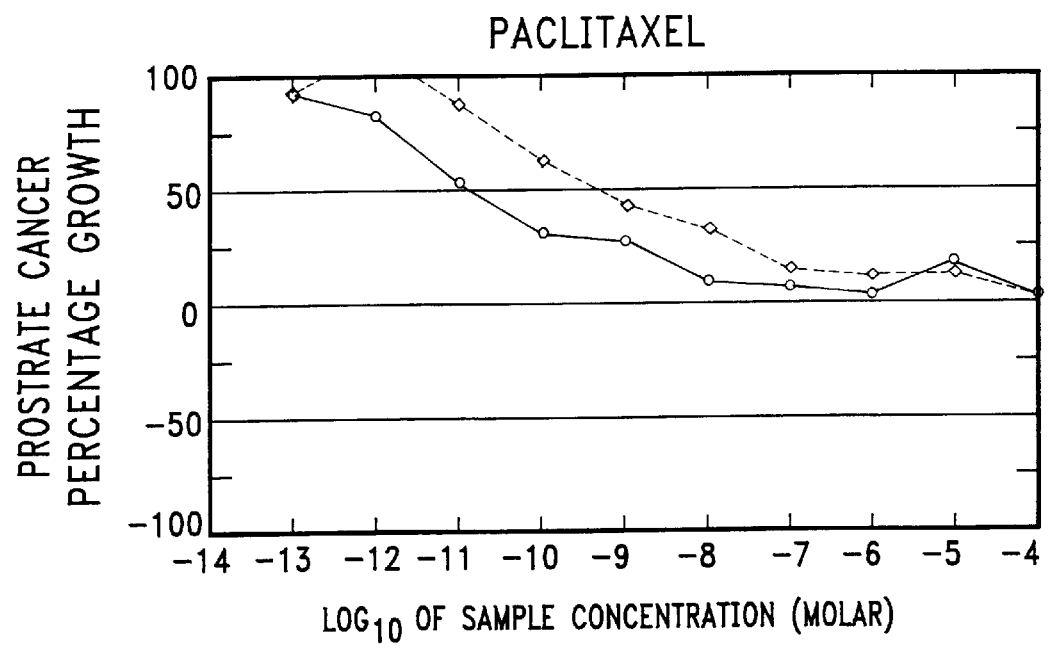
FIG. 8b depicts the dose response curves generated by exposing various prostate cancer cell lines to various concentrations of paclitaxel.
Figure 9A:
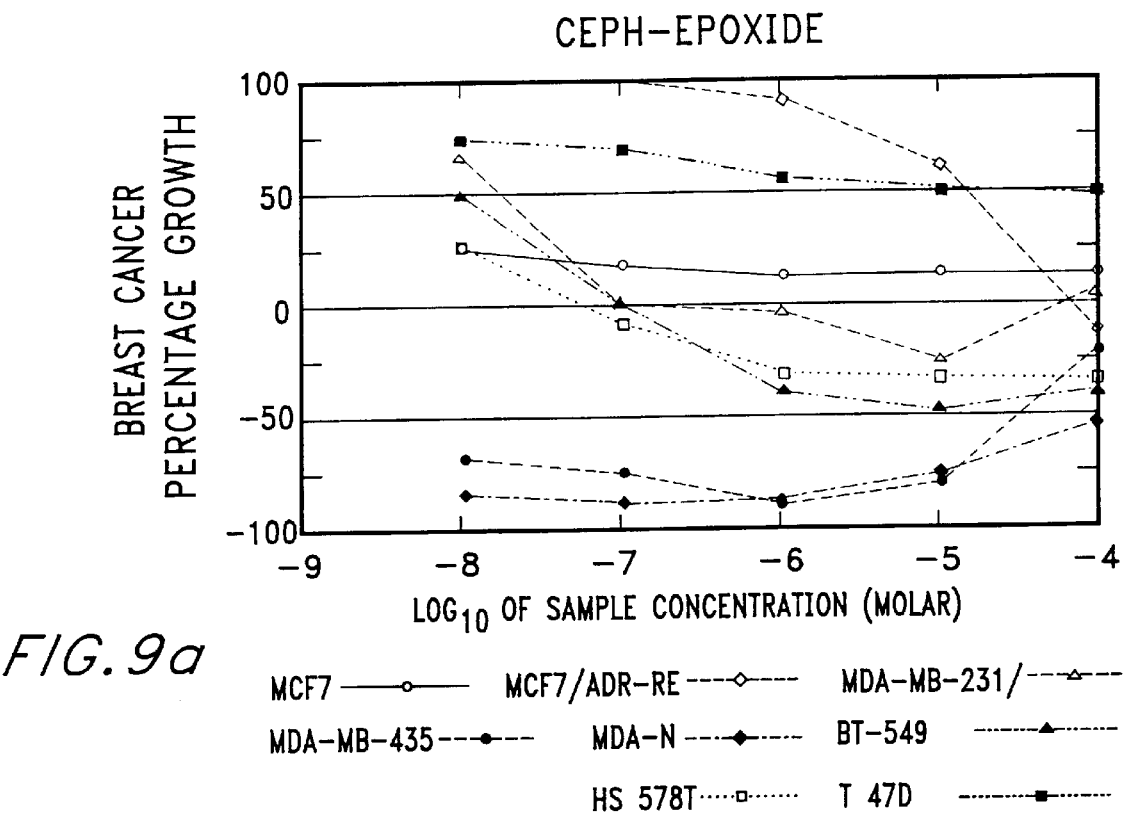
FIG. 9a depicts the dose response curves generated by exposing various breast cancer cell lines to various concentrations of the composition of the present invention.
Figure 9B:
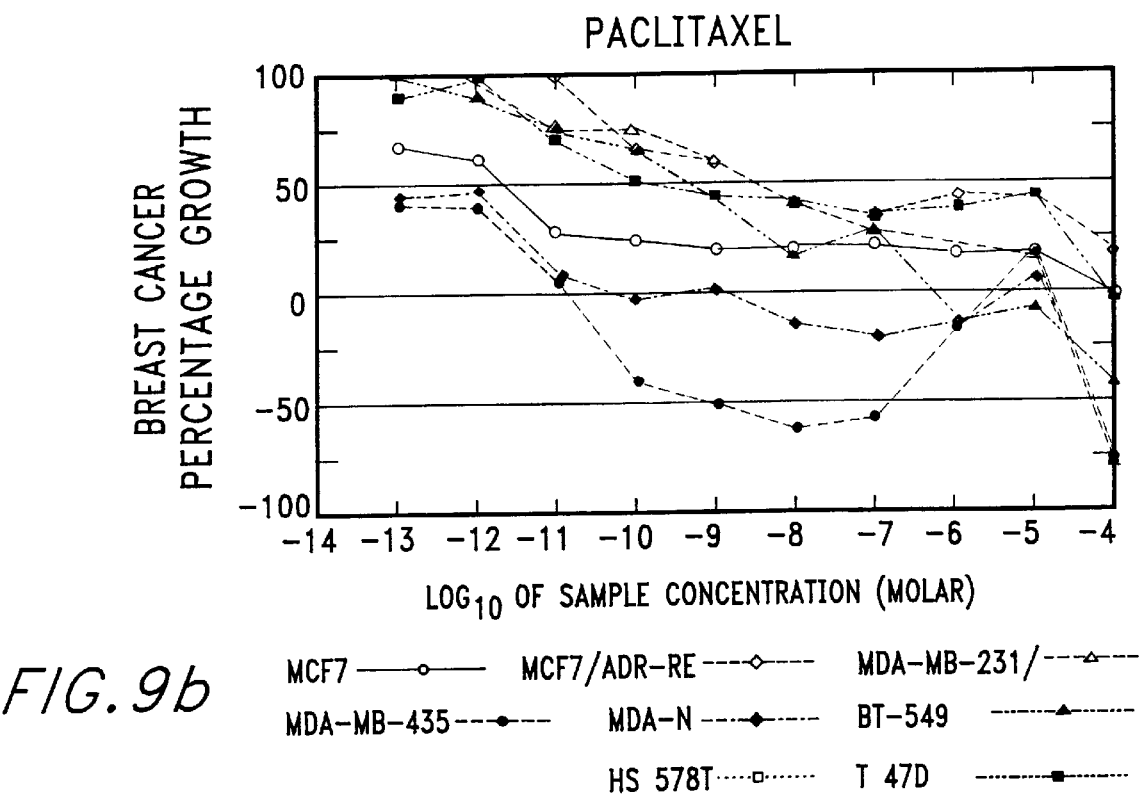
FIG. 9b depicts the dose response curves generated by exposing various breast cancer cell lines to various concentrations of paclitaxel.

Referring to the leukemia cell line CCRF-CEM, in FIGS. 1a and 1b the first comparison that is made between the epoxide of the present invention, ceph-epoxide, and paclitaxel are the concentrations of the two drugs which are necessary to inhibit growth, graphically represented as in FIGS. 1a and 1b as the concentration necessary to achieve the value of +50. As discussed previously, the five drug dilutions routinely tested range from $10^{-4}$ to $10^{-8}$ molar. Therefore, concentrations less than or greater than $10^{-8}$ and $10^{-4}$ molar, that are required to achieve a desired result are not determined. Referring now to FIG. 1a, some concentration less than $10^{-8}$ molar is necessary to achieve primary growth inhibition. The same can be said for paclitaxel, see FIG. 1b; however, the lower concentrations have been determined for this drug and the concentration at which primary growth inhibition occurs using paclitaxel is −11.61 molar. The concentration at which ceph-epoxide is considered cytostasis, i.e. percentage growth is equal to 0, is −5.6 molar, while an equivalent intensity using paclitaxel is achieved at a concentration greater than −4.00 molar. Cytotoxicity, i.e., the concentration for which the percentage growth is equal to −50, occurs for both drugs at some concentration greater than −4.00 molar.

The potency of the epoxide of the present invention as compared to paclitaxel varies from cell line to cell line. However, on the whole the potency ceph-epoxide was found to be equivalent to and in many instances greater than that of paclitaxel's. The mean values for both ceph-epoxide and paclitaxel are listed at the end of the Table I. When interpreting these numbers, however, it is important to take into consideration that values above $10^{-8}$ and below $10^{-4}$ were not collected, this factor is reflected in the range.

The following non-limited examples provide specific high yield processes for preparing cephalomannine epoxide and 10-DATB-epoxide from cephalomannine and 10-DATB, respectively. All scientific and technical terms have the meanings as understood by one with ordinary skill in the art. The specific examples which follow illustrate the synthesis of representative compounds of the instant invention and are not to be construed as limiting the invention in sphere or scope. The methods may be adapted to variation in order to produce compounds embraced by this invention but not specifically disclosed. Further, variations of the methods to produce the same compounds in somewhat different fashion will be evident to one skilled in the art.

All temperatures are understood to be in Centigrade (°C.) when not specified. The nuclear magnetic resonance (NMR) spectral characteristics refer to chemical shifts δ expressed in parts per million (ppm) versus tetramethylsilane (TMS) as reference standard. $^1$H and $^{13}$C NMR spectra were recorded on a Varian Gemini-400 instrument or JEOL Eclipse-400. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiple (m), doublet (d), quartet (q), triplet (t), doublet of doublet (dd), doublet of triplet (dt), and doublet of quartet (dq). The solvents employed for taking NMR spectra are DMSO-$d_6$ (perdeuterodimethysulfoxide), $D_2O$ deuterated water), CDCl$_3$ (deuterochloroform) and other conventional deuterated solvents. The chemical shifts are expressed in ppm relative to the reference of $CDCl_3$ or DMSO. Deuterated solvents were purchased from Aldrich Chemical Co. The infrared (IR) spectral description was measured on a KVB Analect Diamond-20 FT-IR Spectrometer featuring a Laser Precision XAD-Plus Microscope. Electrospray mass spectra were obtained from a VG Platform HPLC-MASS Spectrometer. TLC plates of silica gel 60F254 were purchased from E. M. Merck and kept in a closed container over Drierite® prior to use. Melting points were measured on a MEL-TEMP II apparatus equipped with a digital Barnant 100 Thermocouple Thermometer and are uncorrected. HPLC was performed on a Hitachi chromatographic spectrometer (L-6200A Intelligent Pump, D-6000 Interface, L-4000 UV Detector and AS-4000 Intelligent Auto Sampler). Combination of $CH_3CN$ and $H_2O$ in different concentrations are used as HPLC solvent system. All solvents were distilled before use. Commercially available chemicals were used without any further purification. Various methods of purifying the products of the present invention are known and understood by those skilled in the art and the purification methods presented in the Examples is solely listed by way of example and is not intended to limit the invention.

EXAMPLE I 200 mg (0.24 mmol) of cephalomannine and 5 ml of methylene chloride were introduced under an argon atmosphere into a 25 ml round bottomed flask equipped with a magnetic stir bar. 415 mg (5 eq, 50–60%) of MCPBA was added and the mixture was then stirred at room temperature overnight.

The reaction mixture which was diluted into methylene chloride was then washed with $Na_2S_2O_3$ (20%), $NaHCO_3$ (sat.) and water. The organic phase was collected, dried over magnesium sulfate and subsequently filtered. The solvent was removed under reduced pressure to obtain 197.4 mg of pure ceph-epoxides (two isomers) resulting in a 96.8% yield. $^1H$ NMR(400 MHz, $CDCl_3$) $\delta$8.11 (d, J=8.0 Hz, 4H), 7.61 (m, 2H), 7.50 (t, J=8.0 Hz, 2H), 7.48 (t, J=8.0 Hz, 2H), 7.38 (t, J=8.0 Hz, 4H), 7.37 (t, J=8.0 Hz, 4H), 7.32 (d, J=4.0 Hz, 1H), 7.30 (d, J=4.0 Hz, 1H), 7.19 (d, J=8.0 Hz, 1H), 7.14 (d, J=8.0 Hz, 1H), 6.26 (s, 1H), 6.25 (s, 1H), 6.18 (dd, J=8.0 Hz, 2H), 5.66 (d, J=8.0 Hz, 2H), 5.41 (dd, J=8.0 Hz, 1H), 5.40 (dd, J=8.0 Hz, 1H), 4.93 (m, 2H), 4.60 (bs, 2H), 4.38 (m, 2H), 4.29 (d, J=8.0 Hz, 2H), 4.17 (d, J=8.0 Hz, 2H), 3.78 (d, 1H), 3.76 (d, 1H), 3.44 (d, J=4.0 Hz, 1H), 3.27 (d, J=4.0 Hz, 1H), 3.03 (q, J=4.0 Hz, 1H), 2.97 (q, J=4.0 Hz, 1H), 2.52 (m, 1H), 2.45 (m, 1H), 2.33 (s, 3H), 2.31 (s, 3H), 2.26 (m, 4H), 2.23 (s, 6H), 1.80 (m, 2H), 1.66 (s, 6H), 1.42 (s, 3H), 1.41 (s, 3H), 1.25(s, 6H), 1.14 (s, 6H); $^{13}C$ NMR (100 MHz, $CDCl_3$) $\delta$203.54, 172.66, 172.32, 171.55, 171.09, 170.22, 170.12, 166.89, 141.94, 141.81, 137.72, 137.47, 133.63, 133.22, 133.15, 130.14, 129.20, 129.17, 128.88, 128.64, 128.31, 126.96, 126.89, 84.37, 81.14, 81.08, 78.95, 76.43, 75.54, 74.96, 73.34, 73.27, 73.13, 73.05, 72.23, 72.09, 71.99, 59.98, 59.92, 59.61, 59.55, 54.34, 54.15, 45.67, 43.16, 35.62, 35.54, 26.80, 26.75, 22.53, 22.48, 21.70, 20.73, 14.79, 14.69, 13.46, 12.76, 12.62, 12.56, 9.58, 9.51; MS (electrospray) m/e 848.3 $(M+H)^+$, 865.4 $(M+NH_4)^+$, 870.2 $(M+Na)^+$.

EXAMPLE II 200 mg (0.24 mmol) of cephalomannine and 5 ml of methylene chloride were introduced under an argon atmosphere into a 25 ml round bottomed flask equipped with a magnetic stir bar. 415 mg (1.2 mmol, 5 eq as 50%) of MCPBA was added and the mixture was then stirred at room temperature overnight.

The reaction mixture was then cooled to 0° C. forming a white precipitate. The resulting white precipitate was removed from the mixture and the solvent evaporated to form a residue. The resulting residue was dissolved in 25% ethylacetate/hexane with a few drops of methylene chloride and purified by chromatography on a 10×30 mm silica gel column. The crude mixture was eluted with 25% ethylacetate/hexane followed by 7% methanol/methylene chloride. The 25% ethyl acetate/hexane solution contains MCPBA and the other impurities. The 7% methanol/methylene chloride solution contains the pure mixture of isomers of ceph-epoxide. The selected fractions were evaporated to dryness with a rotary evaporator under reduced pressure to obtain white crystals of pure product. 158 mg of pure ceph-epoxide (two isomers) were recovered resulting in a 78% yield. The resulting product proved to be identical to that obtained in Example I above, as analyzed by TLC and HPLC.

EXAMPLE III 5 mg of cephalomannine and 0.5 ml of methylene chloride were introduced under an argon atmosphere into a 25 ml round bottomed flask equipped with a magnetic stir bar. A large excess (~20 eq) of MMPP was added and the mixture was then stirred at room temperature for three days.

The reaction mixture was then cooled to 0° C. forming a white precipitate. The resulting white precipitate was removed from the mixture and the solvent evaporated to form a residue. The resulting residue was dissolved in 25% ethylacetate/hexane with a few drops of methylene chloride and purified by chromatography on a 10×30 mm silica gel column. The crude mixture was eluted with 25% ethylacetate/hexane followed by 7% methanol/methylene chloride. The 25% ethyl acetate/hexane solution contains MMPP and the other impurities. The 7% methanol/methylene chloride solution contains the pure mixture of isomers of ceph-epoxide. The selected fractions were evaporated to dryness with a rotary evaporator under reduced pressure to obtain white crystals of pure product. The resulting product proved to be identical to that obtained in Example I above, as analyzed by TLC and HPLC and MS.

EXAMPLE IV 100 mg (0.12 mmol) of 10-deacetyl taxol B and 2 ml of methylene chloride were introduced under an argon atmosphere into a 25 ml round bottomed flask equipped with a magnetic stir bar. 207.7 mg (1.2 mmol, 10 eq, 40–60% reagent) of MCPBA was added and the mixture was then stirred at room temperature overnight.

The reaction mixture which as diluted into methylene chloride was then washed with $Na_2S_2O_3$ (20%), $NaHCO_3$ (Sat.) and water. The organic phase was collected, dried over magnesium sulfate and subsequently filter. The solvent was removed under reduced pressure to obtain 65.2 mg of pure 10-DATB (two isomers) resulting in a 64.0% yield. $^1H$ NMR (400 MHz, $CDCl_3$) $\delta$1.09 (s, 3H, C-17-Me, (1.12, s, 3)), 1.22 (s, 3H, C-16-Me), 1.31 (d, J=5.12, 3H, C-7'-Me, (1.34, d, J=5.49 Hz, 3)) 1.44 (s, 3H, C-19-Me), 1.75 (s, 3H, C-18-Me, (1.79, s, 3)), 1.83 (m, 1H, C-6$\beta$), 2.25 (m, 2H, C-14$\alpha$, $\beta$), 2.31 (s, 3H, 4-OAc, (2.33, s, 3)), 2.57 (m, 1H, C-6$\alpha$), 2.99 (q, J=5.49, 1H, C-7'1-H, (3.05, q, J=5.49 Hz, 1H)), 3.32 (d, J=5.85, 1H C-2'-OH, (3.49, d, J=5.85, H1)), 3.89 (br d, J=5.85 Hz, 1H, C-3), 4.19 (d, J=8.78 Hz, 1H, C-20$\beta$), 4.20 (br s, 1H, 10-OH), 4.21 (m, 1H, C-7), 4.31 (d, J=8.78 Hz, 1H, C-20$\alpha$), 4.60 (m, 1H, C-2'), 4.93 (br d, J=9.88 Hz, 1H, C-5), 5.19 (d, J=1.83 Hz, 1H, C-10), 5.43 (dd, J=6.22, 2.93

Hz, 1H, C-3'), 5.68 (d, J=6.95 Hz, 1H, C-2), 6.18 (br t, J=8.05 Hz, 1H, C-13), 7.20 (d, J=9.15 Hz, 1H, C-3'-NH), 7.29–7.64 (m, 8H, aromatic), 8.11 (d, J-7.32 Hz, 2H, C-2-Bz-o); $^{13}C$ NMR (100 MHz, CDCl$_3$) δ9.95, 12.87, 13.66, 14.47, 20.69, 20.95, 22.62, 26.62, 35.86, 37.03, 43.14, 45.00, 46.54, 54.22, 54.41, 57.21, 57.74, 59.47, 59.83, 60.09, 72.06, 72.46, 73.18, 73.46, 74.60, 74.86, 78.79, 79.32, 81.20, 84.23, 127.05, 128.46, 128.79, 129.04, 130.26, 133.82, 136.17, 137.54, 138.26, 167.02, 170.30, 171.65, 172.22, 211.30, MS (electrospray) m/e 806.3 $(M+H)^+$, 823.3 $(M+NH_4)^+$, 828.3 $(M+Na)^+$.

The foregoing description is considered as illustrative only of the principals of the invention. Furthermore, since numerous modifications and changes will readily occur to those skilled in the art, it is not desired to limit the invention to the exact compositions and processes shown as described above. Accordingly, all suitable modifications and equivalents may be resorted to falling within the scope of the invention as defined by the claims which follow.

The embodiments of the invention in which an exclusive property or privilege is claimed are defined as follows:

1. A process for the preparation of a taxane epoxide and its respective isomers which comprises reacting an oxidizing reagent with a compound of formula:

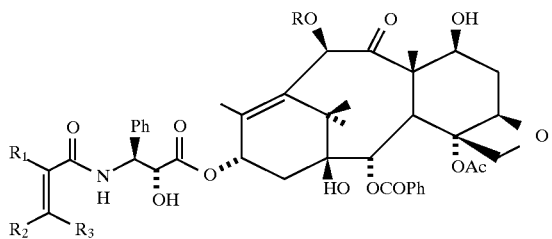

in which R represents an acetyl group or H, $R_1$ and $R_2$ are an alkyl group such as Me, Et, Pr, i-Pr, n-Bu or t-Bu, $R_3$ is H; $R_1$ and $R_2$ and $R_3$ are H; $R_1$ is an alkyl group such as Me, Et, Pr, i-Pr, n-Bu or t-Bu, $R_2$ and $R_3$ are H; $R_1$ and $R_3$ are H, $R_2$ is an alkyl group such as Me, Et, Pr, i-Pr, n-Bu or t-Bu; $R_1$ is H, $R_2$ and $R_3$ are an alkyl group such as Me, Et, Pr, i-Pr, n-Bu or t-Bu; $R_1$ and $R_2$ and $R_3$ are an alkyl group Me, Et, Pr, i-Pr, n-Bu or t-Bu, in an organic solvent at a temperature for a period of time sufficient to produce a product of formula:

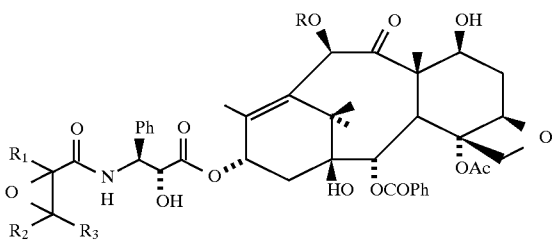

in which R is Ac or H, and $R_1$ and $R_2$ are alkyl, $R_3$ is H; $R_1$ and $R_2$ and $R_3$ are H; $R_1$ is alkyl, $R_2$ and $R_3$ are H; $R_1$ and $R_3$ are H, $R_2$ is alkyl; $R_1$ is H, $R_2$ and $R_3$ are alkyl; $R_1$ and $R_2$ and $R_3$ are alkyl.

2. The process of claim 1, wherein R is Ac, $R_1$ and $R_2$ are Me, $R_3$ is H.

3. The process of claim 1, wherein R is H, $R_1$ and $R_2$ are Me, $R_3$ is H.

4. The process of claim 1, wherein said organic solvent is methylene chloride.

5. The process of claim 2, wherein oxidizing reagent is used at a reaction temperature of 0°–50° C.

6. The process of claim 5, wherein said oxidizing reagent is 3-chrolorperoxybenzoic acid.

7. The process of claim 6, wherein said period of time is about 12–24 hours.

8. The process of claim 5, wherein said oxidizing reagent is monoperoxyphethalic acid magnesium salt hexahydrate.

9. The process of claim 8, wherein said period of time is about 72 hours.

10. A compound having anticancer activity of formula:

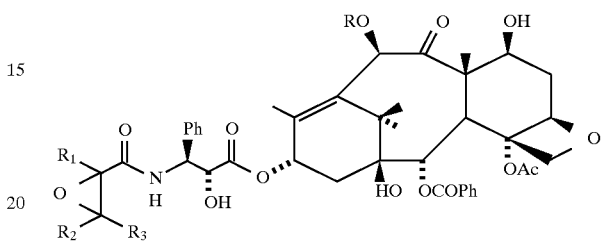

wherein R represents an acetyl group and $R_1$ is an alkyl group (AC) or hydrogen (H); $R_2$ is an alkyl group or hydrogen; and $R_3$ is an alkyl group or hydrogen.

11. The compound of claim 10, wherein $R_1$ and $R_2$ and $R_3$ are H.

12. The compound of claim 10, wherein $R_1$ is Me, and $R_2$ and $R_3$ are H.

13. The compound of claim 10, wherein $R_1$ and $R_3$ are H, and $R_2$ is Me.

14. The compound of claim 10, wherein $R_1$ is H, and $R_2$ and $R_3$ are Me.

15. The compound of claim 10, wherein $R_1$ and $R_2$ and $R_3$ are Me.

16. A compound having anticancer activity of formula:

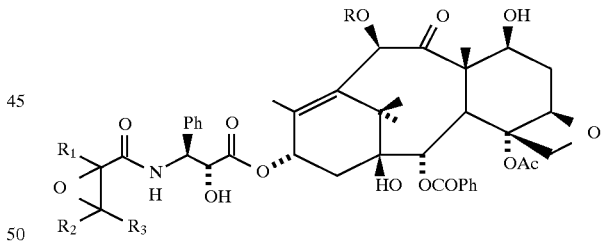

wherein R represents hydrogen and $R_1$ is an alkyl group (Ac) or hydrogen (H); $R_2$ is an alkyl group or hydrogen; and $R_3$ is an alkyl group or hydrogen.

17. The compound of claim 16, wherein $R_1$ and $R_2$ and $R_3$ are H.

18. The compound of claim 16, wherein $R_1$ is Me, and $R_2$ and $R_3$ are H.

19. The compound of claim 16, wherein $R_1$ and $R_3$ are H, and $R_2$ is Me.

20. The compound of claim 16, wherein $R_1$ is H, and $R_2$ and $R_3$ are Me.

21. The compound of claim 16, wherein $R_1$ and $R_2$ and $R_3$ are Me.

22. A compound having anticancer activity of formula:
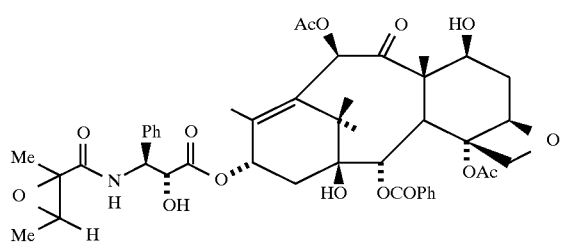
23. A compound having anticancer activity of formula:
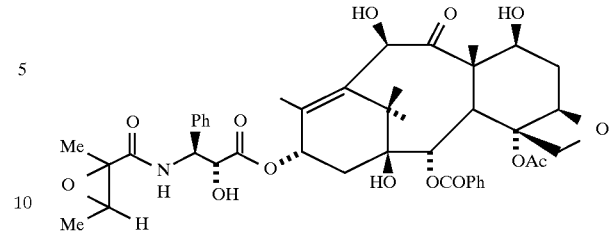
* * * * *